United States Patent [19]
Dixon et al.

[11] Patent Number: 5,470,882
[45] Date of Patent: Nov. 28, 1995

[54] ANTI-INFLAMMATORY COMPOUNDS

[75] Inventors: James S. Dixon, Malvern; Raplh F. Hall, Villanova; Lisa A. Marshall, Wyndmoor, all of Pa.; Floyd H. Chilton, III, Pilot Mountain, N.C.; Ruth J. Mayer, Wayne; James D. Winkler, Fort Washington, both of Pa.

[73] Assignee: SmithKline Beecham Corp., Philadelphia, Pa.

[21] Appl. No.: 252,716

[22] Filed: Jun. 2, 1994

[51] Int. Cl.$^6$ .................................................. A01N 47/28
[52] U.S. Cl. ........................... 514/596; 514/598; 562/41; 562/48
[58] Field of Search ................ 562/41, 48; 514/596, 514/598

[56] References Cited

U.S. PATENT DOCUMENTS

| | | | |
|---|---|---|---|
| 2,119,882 | 6/1938 | Kraeker et al. | 562/58 |
| 2,141,893 | 12/1938 | Zitscher et al. | 562/55 |
| 2,299,834 | 10/1942 | Martin et al. | 562/47 |
| 2,311,062 | 2/1943 | Martin et al. | 562/48 |
| 2,328,159 | 8/1943 | Martin et al. | 554/45 |
| 2,363,074 | 11/1944 | Martin et al. | 562/48 |
| 2,424,477 | 7/1947 | Martin et al. | 562/66 |
| 2,649,476 | 8/1953 | Martin | 562/48 |
| 2,722,544 | 11/1955 | Martin | 562/48 |
| 2,760,958 | 8/1956 | Bossard et al. | 534/673 |
| 3,055,930 | 9/1962 | Graf et al. | 560/12 |
| 3,674,843 | 7/1972 | Shen et al. | 562/430 |
| 3,927,093 | 12/1975 | Yale | 564/430 |
| 4,005,141 | 1/1977 | Moore et al. | 564/97 |
| 4,250,192 | 2/1981 | Sallmann et al. | 514/533 |
| 4,528,392 | 7/1985 | Musser et al. | 560/43 |
| 4,897,397 | 1/1990 | Shih et al. | 514/277 |

FOREIGN PATENT DOCUMENTS

| | | |
|---|---|---|
| 997176 | 7/1965 | United Kingdom . |
| 1027060 | 4/1966 | United Kingdom . |

*Primary Examiner*—José G. Dees
*Assistant Examiner*—Joseph M. Conrad, III
*Attorney, Agent, or Firm*—Dara L. Dinner; Stephen Venetianer; Edward T. Lentz

[57] ABSTRACT

This invention relates to the novel pharmaceutical compositions of Formulas (I) and (II) each of which comprises a compound of Formula (I) or (II) and a pharmaceutically acceptable diluent or carrier.

This invention also relates to a method of treating or reducing inflammation in a mammal in need thereof, which comprises administering to said mammal an effective amount of a compound or composition of Formula (I) or (II).

5 Claims, No Drawings

ANTI-INFLAMMATORY COMPOUNDS

FIELD OF THE INVENTION

This invention relates to pharmaceutical compositions and their use as anti-inflammatory agents in mammals.

BACKGROUND OF THE INVENTION

An early event in the response of most inflammatory cells to immunologic activation and other stimuli is the release of newly formed products (mediators) which alter the function and biochemistry of surrounding cells and tissues. The ensuing biological responses, as well as much of the pathogenesis which is attributed to inflammation and allergy, are thought to be dependent on the effects that these newly-formed mediators have on adjacent cells within the inflammatory region.

In the last 20 years, it has become apparent that lipid mediators are among the most potent and important products which are generated during inflammatory reactions. The synthesis of most lipid mediators is initiated by the specific cleavage of complex phospholipid molecules which contain arachidonate at their sn-2 position. Arachidonic acid is predominantly found in the sn-2 position of phospholipids after redistribution by transacylases and its release by sn-2 acylhydrolases from phospholipids represents the rate-limiting step in the formation of eicosanoids (leukotrienes, prostaglandins and thromboxanes) and other hydroxylated fatty acids. As arachidonic acid is released, it is then converted to oxygenated derivatives by at least two enzymatic systems (lipoxygenase and/or cyclooxygenase). Concomitant with arachidonate release, lysophospholipids are formed. One of these lyso phospholipids, 1-alkyl-2-lyso-sn-glycero-3-phosphocholine, is then acetylated to form platelet-activating factor (PAF). Each of the cell types involved in the inflammatory response produce and secrete a unique subset of lipid mediators. The quantities and nature of the metabolites depend on which enzymes and precursor phospholipid pools are available to inflammatory cells.

Once lipid mediators such as PAF and eicosanoids are formed by the aforementioned pathways, they induce signs and symptoms observed in the pathogenesis of various inflammatory disorders. Indeed, the pathophysiological activity of arachidonic acid (and its metabolites) is well known to those skilled in the art. For example, these mediators have been implicated as having an important role in allergy, asthma, anaphylaxis, adult respiratory distress syndrome, reperfusion injury, inflammatory bowel disease, rheumatoid arthritis, endotoxic shock, and cardiovascular disease. Aalmon et al., Br. Med. Bull (1978) 43:285–296; Piper et al., Ann. New York Acad. Sci. (1991) 629:112–119; Holtzman, Am. Rev. Respir. Dis. (1991) 143:188–203; Snyder, Am. J. Physiol. Cell Physiol. (1990) 259:C697–C708; Prescott et al., J. Biol. Chem. (1990) 265:17381–17384.

Similar to arachidonate products, PAF is a potent proinflammatory mediator produced by a variety of cells. In vitro, PAF stimulates the movement and aggregation of neutrophils and the release therefrom of tissue-damaging enzymes and oxygen radicals. PAF has also been implicated in activation of leukocytes, monocytes, and macrophages. These activities contribute to the actions of PAF as having (pathological) physiological activity in inflammatory and allergic responses. PAF has also been implicated in smooth muscle contraction, pain, edema, hypotensive action, increases in vascular permeability, cardiovascular disorders, asthma, lung edema, endotoxin shock, and adult respiratory distress syndrome. PAF elicits these responses either directly through its own cellular receptor(s) or indirectly by inducing the synthesis of other mediators.

Accordingly, a method which antagonises the production of free arachidonic acid, its metabolites or PAF will have clinical utility in the treatment of a variety of allergic, inflammatory and hypersecretory conditions such as asthma, arthritis, rhinitis, bronchitis and urticaria, as well as reperfusion injury and other disease involving lipid mediators of inflammation. Many published patent applications or issued US patents exist which describe various compounds having utility as PAF or eicosanoid antagonists. Such patents include U.S. Pat. Nos. 4,788,205, 4,801,598, 4,981,860, 4,992,455, 4,983,592, 5,011,847, 5,019,581 and 5,002,941.

Phospholipase A2's ($PLA_2$, (EC 3.1.1.4)) are responsible for the liberation of arachidonic acid from the sn-2 position of phospholipid. They are therefore thought to play an important role in the pathogenesis of inflammation and possibly in immunological dysfunction, both as a cell associated enzyme as well as an extracellular soluble enzyme. Low molecular weight, mammalian Type II 14 kDa $PLA_2$ has been well characterized and is known to exist in both an extracellular form in inflammatory fluids (Kramer et at., J. Biol. Chem., 264:5768–5775 (1989)) and in a cell associated form (Kanda et al., Biochemical and Biophysical Research Communications, 163:42–48 (1989)) and has been found in a variety of cells and tissues or extracellularly when released in response to antigenic activators or pro-inflammatory mediators such as Interleukin (IL)-1, IL-6 or tumor necrosis factor (TNF). Its presence in such inflammatory fluids, tissue exudates or serum has therefore implicated Type II14 kDa-$PLA_2$'s role in inflammation (Vadas, et at., (1985) Life Sci. 36, 579–587; and Seilhamer, et at., (1989) J. Biol. Chem. 264, 5335–5338). Recently, the elevated serum levels of $PLA_2$ activity during an inflammatory insult has been attributed to cytokine induction of acute phase protein release from liver, of which the 14 kDa-$PLA_2$ is suggested to be a part (Crowl, et al., (1991) J. Biol. Chem. 266, 2647–2651). In addition, soluble $PLA_2$ activity is markedly elevated in the serum and synovial fluid of patients with rheumatoid arthritis (Stefanski et at., J. Biochem. 100:1297–303 (1986). Furthermore, increasing serum $PLA_2$ levels have been shown to positively correlate with clinical severity (Bomalaski and Clark, Arthritis and Rheumat. 36:190–198 (1993)). Various inhibitors of $PLA_2$ have been described in publications and in U.S. Patents. See for instance U.S. Pat. Nos. 4,959,357; 4,933,365; 5,208,223; 5,208244; Marshall et al., J. Rheumatology 18:1 (1991 ); Marshall et at., Phospholipase A2, Ed. Pyu Wong, Plenum Press, New York (1990) pages 169–181; Wilkerson, et at., Eur. J. Med. Chem., 26:667, 1991 and Wilkerson, Antiinflammatory Phospholipase $A_2$ Inhibitors, Drugs of the Future, Vol. 15, No. 2 p 139–148(1990). Accordingly, as $PLA_2$ is important in the liberation of arachidoninc acid from phospholipid and may also play a role in the generation of PAF via lysophospholipid formation, inhibition of such an enzyme would be useful for the treatment of disease states caused thereby.

There are many novel forms of phospholipase $A_2$'s which have recently been discovered. For the purposes herein, members of the sn-2 acylhydrolase family of $PLA_2$'s are divided into low and high molecular weight enzymes be it from mammalian, or non-mammalian sources. Low molecular weight $PLA_2$'s will generally have a molecular weight in the range of 12,000 to 15,000. High molecular weight will be in the range of 30,000 or 56,000 kDa to 110,000 by SDS electrophoresis analysis.

A high molecular weight, cytosolic 85 kDa $PLA_2$ has been isolated and cloned from the human moncytic cell line, U937 (Clark et al., Proc. Natl. Acad. Sci., 87:7708–7712, 1990). The cell-associated Type II-14 kDa-$PLA_2$ in cell lipid metabolism was thought to be the key rate limiting enzyme in lipid mediator formation, until the recent identification of this cell-associated but structurally distinct 85 kDa sn-2 acylhydrolase, (Clark, et al., supra); and Kramer, et al., (1991) J. Biol. Chem. 266, 5268–5272. Like the Type II-14 kDa enyzme, this enzyme is active at neutral pH and $Ca^{2+}$-dependent, but in contrast exhibits a preference for AA in the sn-2 position of phospholipid substrate and migrates from the cytosol to the membrane in a $Ca^{2+}$-dependent manner and is regulated by phosphorylation (Kramer et al., J. Biol. Chem., 266:5268–5272 (1991). The 85 kDa-$PLA_2$ is also distinct from 14 kDa-$PLA_2$s and $Ca^{2+}$-independent $PLA_2$ as demonstrated by different biochemical characteristics such as stability of the 85 kDa-$PLA_2$ to DTT, instability to heat and the lack of inhibition by a phosphonate phospholipid TSA inhibitor of 14 kDa-$PLA_2$. In addition, 85 kDa-$PLA_2$ has been shown to possess a lysophospholipase $A_1$ activity which is not observed with the 14 kDa-$PLA_2$s. The 85 kDa enzyme is similar to the myocardial $Ca2+$-independent $PLA_2$ (Hazen and Gross, Circ. Res. 70:486–495 (1992)) in that $Ca^{2+}$ is not required for catalysis and DTNB inhibition is observed. However, 85 kDa-$PLA_2$ is not inhibited by the suicide inactivator bromoenol lactone, suggesting that the enzyme is distinct from the myocardial enzyme as well. These characteristics make the 85 kDa-$PLA_2$ a candidate for participation in the liberation of AA from phospholipid stores for subsequent metabolism to lipid mediators. Both the cytosolic 85 kDa $PLA_2$ and a cell associated Type II 14 kDa $PLA_2$ have been found in the human immune cells such as monocyte, neutrophil and platelet (Marshall and Roshak, Biochem. Cell Biol. 71:331–339 (1993)). As noted above most of the cellular lipid mediators found elevated in a variety of inflammatory fluid were formed in response to non-pancreatic $PLA_2$ action.

Since arachidonate-containing phospholipids are the key precursors for a broad range of lipid mediators it would not be surprising that, inflammatory cells would treat these phospholipids differently than other fatty acid-containing phospholipids. In particular, there are enzymes which control the mount of arachidonate in different phospholipid pools and these enzymes are tightly regulated to maintain arachidonate homeostasis. The movement of arachidonate into and from all phospholipids was originally thought to be exclusively by Coenzyme A-dependent acyl transferase activitites. Holub et al., Adv. Lipid Res., 16:1–125 (1978); Lands et al., In The Enzymes of Biological Membranes, ed. Martonosi, A., pp. 3– 85, Plenum Press, New York, 1976. However, it has now been demonstrated that an enzyme, Coenzyme A-independent transcylase (CoA-IT), is involved in the movment of 20 carbon higher unsaturated fatty acids, particularly arachidonate, into particular (1-alkyl- and 1-alkenyl)phospholipid pools. These are the phospholipid pools of arachidonate that are preferentially mobilized during cell activation and utilized for eicosanoid and PAF biosynsthesis, respectively.

CoA-IT has a specificity for certain phospholipids as donor and acceptor molecules. The fatty acid transferred is long chained and unsaturated, and almost exclusively arachidonate. Other fatty acids such as the 16:0, 18:1 or 18:2 are not moved into the sn-2 position of alkyl and 1-alkenyl phospholipid pools by CoA-IT. The specificity of CoA-IT is in direct contrast to many other CoA-dependent acylation activities which acylate a wide variety of lysophospholipids with no selectivity for arachidonate.

Accordingly, as CoA-IT is involved in arachidonic acid and phospholipid metabolism, inhibition of such an enzyme would be useful for the treatment of inflammatory, allergic and hypersecretory conditions or disease states caused thereby. Therefore, a method by which CoA-IT is inhibited will consequently and preferentially decrease the arachidonate content of 1-alkyl- and 1-alkenyl-linked phospholipids and will therefore decrease the production of pro-inflammatory mediators such as free arachidonic acid, prostaglandins, leukotriene and PAF during an inflammatory response.

SUMMARY OF THE INVENTION

This invention relates to a pharmaceutical compositions of Formula (I) comprising a compound of Formula (I), or pharmaceutically acceptable salt thereof and a pharmaceutically acceptable diluent or carrier.

The present invention also provides for a pharmaceutical composition comprising a pharmacuetically acceptable carrier or diluent and a compound, or pharmaceutically acceptable salt thereof, of Formula (II).

This invention also relates to a method of treating or reducing inflammation in a mammal in need thereof, which comprises administering to said mammal an effective amount of a compound or composition of Formula (I) or Formula (II).

This invention also relates to a method of treating disease or disorders mediated by $PLA_2$ and/or CoA-IT, free arachidonic acid, its metabolites and/or PAF by administering to a patient in need thereof, an effective amount of a compound of Formula (I) or Formula (II).

This invention also relates to a method of treating disease or disorders mediated by phospholipase $A_2$ and/or CoA-IT, by administering to a patient in need thereof, an effective amount of a compound or composition of Formula (I) or Formula (II).

One aspect of the present invention is a pharmaceutical composition comprising a pharmaceutically acceptable carrier or diluent and a compound represented by the structure corresponding to the formula:

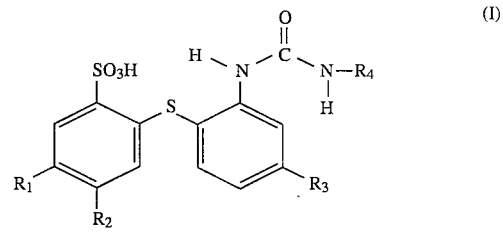

wherein $R_4$ is a phenyl subsiuted one to two times independently with chlorine or $CF_3$;

$R_1$ is chlorine;

$R_2$ is hydrogen or chlorine;

$R_3$ is chlorine or $CF_3$;

provided that when $R_1$ and $R_2$ are both chlorine then $R_3$ is $CF_3$;

and pharmaceutically acceptable salts thereof.

Another aspect of the present invention is a pharmaceutical composition comprising a pharmaceutically acceptable carrier or diluent and a compound represented by the structure corresponding to the formula:

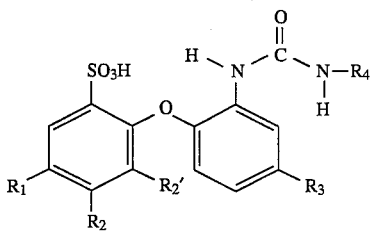

wherein

R$_4$ is a phenyl substituted one to two times independently with chlorine or CF$_3$ or R$_4$ is a disubstituted phenyl substituted once by chlorine or CF$_3$ and once by 3-chlorophenoxy or a 4-chlorophenoxy group;

R$_1$ is chlorine or —C((CH$_3$)$_2$)CH$_2$CH$_3$;

R$_2$ is hydrogen, chlorine or methyl;

R$_2$' is hydrogen or chlorine;

R$_3$ is chlorine or CF$_3$;

provided that a) when R$_2$ is methyl, then R$_1$ and R$_3$ are both chlorine and R$_4$ is a 3-CF$_3$-4-chlorophenyl, 3,4-dichlorophenyl, or 2-methyl-6-chlorophenyl;

b) when R$_1$ is t-amyl then R$_2$ and R$_2$' are hydrogen;

c) when R$_1$ is t-amyl, R$_2$ and R$_2$' are hydrogen, and R$_3$ is CF$_3$, then R$_4$ is 3-CF$_3$-phenyl, 3,5-bis(trifluoromethyl)phenyl or 4-chloro-3-CF$_3$ phenyl;

d) when R$_2$' is chlorine, then R$_2$ is hydrogen, R$_1$ and R$_3$ are both chlorine and R$_4$ is 2-methyl-4-chlorophenyl;

e) when R$_1$ and R$_3$ are chlorine, and R$_2$ and R$_2$' are hydrogen, then R$_4$ is 2,5-dichlorophenyl, 3,5-ditrifluoromethyl phenyl, 2-chloro-5-CF$_3$-phenyl, 3-CF$_3$-4-chlorophenyl, 3,4-dichlorophenyl, 2,3-dichlorophenyl, 4-chlorophenyl, 3-trifluoromethylphenyl, 3-chloro-4-(4-chlorophenoxy), 3-CF$_3$-6-(4-chlorophenoxy), 3-chloro-6-(4-chlorophenoxy);

f) when R$_1$, R$_2$ and R$_3$ is chlorine, then R$_4$ is 2-chloro-5-CF$_3$-phenyl or 3-CF$_3$-4-chlorophenyl;

g) when R$_1$ and R$_2$ are chlorine, and R$_3$ is CF$_3$, then R$_4$ is 4-chloro-3-CF$_3$phenyl;

and pharmaceutically acceptable salts thereof.

DETAILED DESCRIPTION OF THE INVENTION

The present invention is directed to a novel method of treating inflammatory disease in a mammal in need thereof by administering to said mammal an effective amount of a compound according to Formula (I) or Formula (II). The compounds of Formula (I) and (II) may selectively inhibit the PLA$_2$ enzyme, the CoA-IT enzyme or both. Inhibition of either or both enzymes will result in the treatment of inflammatory occurrences in mammals. Inflammatory states in mammals may include, but are not limited to, allergic and asthmatic manifestations, dermatological diseases, inflammatory diseases, collagen diseases, reperfusion injury and stroke. Treatment of both acute and chronic diseases are possible. Preferred diseases for treatment are arthritis, asthma, allergic rhinitis, inflammatory bowel disease (IBD), psoriasis, reperfusion injury and stroke. For the purposes herein, the compounds of Formula (I) and (II) are preferential and selective inhibitors of the low molecular weight PLA$_2$ enzyme.

For purpoeses herein, the compounds of the generic formulas (I) and (II), for the (R$_2$)$_m$ term provisos, etc. are numbered by the point of attachment to the ether or thioether. This point of attachment is the one position, the R$_1$ term is the 2-position, etc. The nomenclature used for naming the pecifically exemplified compounds, such as common or IUPAC corresponds to actual rules of nomenclature as is uneffected by the generic formula herein.

Specifically exemplified compounds of Formula (I) are:

4,5-Dichloro-2-[4-trifluoromethyl-2-(3-trifluoromethyl-4-chlorophenyl)ureido)phenyl)thio]benzenesulfonic acid;

4,5-Dichloro-2-[3-(3,4-dichlorophenyl)ureido]-4-trifluoromethylphenyl)thiobenzenesulfonic acid;

5-Chloro-2-[2-(3-(3,5-di-trifluoromethylphenyl)ureido)-4-trifluoromethylphenyl)thio]benzenesulfonic acid;

5-Chloro-2-[(4-chloro-2-(3-(5-chloro-3-trifluoromethylphenyl)ureido)phenyl)thio]benzenesulfonic acid;

5-Chloro-2-[(4-chloro-2-[3-(2,4-dichlorophenyl)ureido)phenyl)thio]benzenesulfonic acid;

5-Chloro-2-[(4-chloro-2-(3-(4-chloro-3-trifluoromethylphenyl)ureido)phenyl)thio]benzenesulfonic acid.

Specifically exemplified compounds of Formula (II) are:

5-Chloro-2-[(4-chloro-2-(3(2,5-dichlorophenyl)ureido)phenyloxy]benzenesulfonic acid;

4,5-Dichloro-2-[4-chloro-2-[[[[2-chloro-5-(trifluoromethyl)phenyl]-amino]carbonyl]amino]phenoxy]benzenesulfonic acid;

5-Chloro-2-[4-chloro-2-[[[[4-chloro-3-(trifluoromethyl)phenyl]amino]carbonyl]amino] phenoxy]-4-methylbenzenesulfonic acid;

5-Chloro-2[(4chloro-2-[3(3,4-dichlorophenyl)ureido)phenyloxy]-4-toluenesulfonic acid;

2-[2-[3-(4-Chloro-2-tolyl)ureido]-4-chlorophenoxy]-3,5-dichlorobenzenesulfonic acid;

2-[2-[3-(4-Chloro-3-trifluoromethylphenyl)ureido] -4-trifluoromethylphenoxy]-4,5-dichlorobenzene sulfonic acid;

2-[2-[[[[3,5-Bis(trifluoromethyl)phenyl]amino]carbonyl] amino]-4-chlorophenoxy]-5 -chlorobenzene acid;

5-(1,1-Dimethylpropyl)-2-[4-(trifluoromethyl)-2-[[[[3 -(trifluoromethyl)phenyl]amino]carbonyl]amino]-phenoxy] benzenesulfonic acid;

2-[2-[3-(4-Chloro-3-trifluoromethylphenyl)ureido]-4 -trifluoromethylphenoxy]-5-(1,1-dimethylpropyl)benzenesulfonic acid;

2-[2-[[[[3,5-Bis(trifluoromethyl)phenyl]amino]carbonyl] amino]-4-(trifluoromethyl)phenoxy]-5-(1,1-dimethylpropyl)benzenesulfonic acid;

4,5-Dichloro-2-[4-chloro-2-[[[[4-chloro-3-(trifluoromethyl)phenyl]amino] carbonyl]amino]phenoxy]benzenesulfonic acid;

5-Chloro-2-[4-chloro-2-[[[[2-chloro-5-(trifluoromethyl)phenyl]amino]carbonyl]amino]phenoxy]benzenesulfonic acids.

5-Chloro-2-[4-chloro-2-[[[[4-chloro-3-(trifluoromethyl)phenyl]amino]carbonyl]amino]phenoxy]benzenesulfonic acid;

5-Chloro-2-(4-chloro-2-(3,4-dichlorophenylaminocarbonylaminophenoxy)benzene sulfonic acid;

5-Chloro-2-(4-chloro-2-(2,3-dichlorophenylaminocarbonylaminophenoxy)benzene sulfonic acid;

5-Chloro-2-(4-chloro-2-(4-chlorophenylaminocarbonylaminophenoxy)benzene sulfonic acid;

5-Chloro-2-(4-chloro-2-(3-trifluoromethylphenylaminocarbonylaminophenoxy)benzene sulfonic acid;

5-Chloro-2-[4-chloro-2-(2-chloro-5-trifluoromethylphenylamino)carbonylamino] phenoxybenzene sulfonic acid;

5-Chloro-2-(4-chloro-2-(3-chloro-4-(4-chlorophenoxy)-phenylaminocarbonylamino)phenyoxybenzene sulfonic acid;

5-Chloro-2-(4-chloro-2-(2-(3-chlorophenoxy)-5 -trifluoromethylphenylaminocarbonylamino)phenyoxybenzene sulfonic acid;

5-Chloro-2-[4-chloro-2-(5-chloro-2-(4-chlorophenoxy)phenylaminocarbonylamino)phenoxy]benzene sulfonic acid.

Another aspect of the present invention for use as $PLA_2$ and/or CoA-IT inhibitors in the treatment of inflammatory conditions am the novel compounds and pharmacuetically acceptable salts thereof:

5-(1,1-Dimethylpropyl)-2-[4-(trifluoromethyl)-2-[[[[3-(trifluoromethyl)phenyl]amino] carbonyl]amino]-phenoxy]benzenesulfonic acid;

2-[2-[3-(4-Chloro-3-trifluoromethylphenyl)ureido]-4-trifluoromethylphenoxy]-5-(1,1-dimethylpropyl)benzenesulfonic acid; and 2-[2-[[[[3,5-Bis(trifluoromethyl)phenyl]amino]carbonyl]amino]-4-(trifluoromethyl)phenoxy]-5-(1,1-dimethylpropyl)benzenesulfonic acid Preferably the pharmaceutically acceptable salts are of the alkali metals, such as sodium.

SYNTHETIC CHEMISTRY

Compounds of Formula (I) and (II) can be readily prepared by one skilled in the art in an analagous manner to the synthesis as indicated below. Alternatively, the compounds specifically exemplified above, except for 2-[2-[3-(4-Chloro-3-trifluoromethylphenyl)ureido]-4-trifluoromethylphenoxy]-5-(1,1-dimethylpropyl)benzenesulfonic acid; 5-(1,1 -Dimethylpropyl)-2-[4-(trifluoromethyl)-2-[[[[3-(trifluoromethyl)phenyl]amino]carbonyl]amino]-phenoxy]benzenesulfonic acid and 2-[2-[[[3,5-Bis(trifluoromethyl)phenyl]amino]carbonyl]amino]-4-(trifluoromethyl)-phenoxy]-5-(1,1-dimethylpropyl)benzenesulfonic acid can be purchased through the BADER catalog of ALDRICH Chemical Company upon request.

Without further elaboration, it is believed that one skilled in the art can, using procedures analagous to those described herein, utilize the present invention to its fullest extent. The invention will now be described by reference to the following examples which are merely illustrative and are not to be construed as a limitation of the scope of the present invention. Temperatures are recorded in degrees centigrade unless otherwise noted.

Example 1

2-[2-[3-(4-Chloro-3-(trifluoromethyl)phenyl]ureido]-4-(trifluoromethyl)phenoxy]-4,5-dichlorobenzenesulfonic acid, sodium salt a) 2-(2-Nitro-4-trifluoromethylphenoxy)-4,5-dichlorobenzene A mixture of 3,4-dichlorophenol (25 gram (hereinafter g), 0.153 mol), 4-chloro-3 -nitrobenzo-trifluoride (52 g, 0.23 mol) and potassium carbonate (63 g, 0.459 mol) in dimethylformamide (450 mL) was stirred under argon at 120° C. for 24 h. The reaction mixture was filtered and the filtrate evaporated. The residue was dissolved in ethyl acetate, washed with water, brine, dried over anhydrous magnesium sulfate, filtered and evaporated. The residue was flash chromatographed (silica gel, methylene chloride/hexane), to give the title compound as a yellow oil.

b) 2-(2-Nitro-4-trifluoromethylphenoxy)-4,5-dichlorobenzenesulfonic acid, ammonium salt Fuming sulfuric acid (8 mililiter (hereinafter mL) was cooled to −20° C. and 2-(2-nitro-4-trifluoromethyl-phenoxy)-4,5-dichlorobenzene (8 g, 22.8 mmol) in methylene chloride (8 mL) was added to the solution. The mixture was stirred for 15 min and then quenched in ice. Extraction with ethyl acetate followed by flash chromatography (silica gel, methylene chloride/isopropanol/ammonium hydroxide) gave the title compound. $^1$H NMR (400 MH$_z$, CD$_3$OD) δ8.31 (d, 1H), 8.11 (s, 1H), 7.87 (dd, 1H), 7.4 (s, 1H), 7.16 (d, 1H).

c) 2-(2-Amino-4-trifluoromethylphenoxy)-4,5-dichlorobenzenesulfonic acid

The 2-(2-nitro-4-trifluoromethylphenoxy)-4,5-dichlorobenzenesulfonic acid, ammonium salt (5 g, 11.2 mmol) was dissolved in acetic acid (75 mL). The mixture was diluted with water (75 mL), and a 20 % aqueous solution of titanium trichloride (65 mL) was added. After aqueous workup the crude product was flash chromatographed (silica gel, methylene chloride/ethanol/ammonium hydroxide) to give the title compound. $^1$H NMR (400 MH$_z$, CD$_3$OD) δ8.02 (s, 1H), 7.17 (d, 1H), 7.12 (d, 1H), 6.94 (dd, 1H), 6.87 (s, 1H).

d) 2-[2-[3(4-Chloro-3-(trifluoromethyl)phenyl]ureido]-4-(trifluoromethyl)phenoxy]-4,5 -dichlorobenzenesulfonic acid, ammonium salt A solution of 2-(2-amino-4-trifluoromethylphenoxy)-4,5-dichlorobenzenesulfonic acid (2 g, 4.8 mmol) and 4-chloro-3-trifluoromethylphenyl isocyanate (1.11 g, 5 mmol) in pyridine (20 mL) was stirred under argon for 72 hours (hereinafter h). The solvent was evaporated and the residue was flash chromatographed (silica gel, methylene chloride/ethanol/ammonium hydroxide) to give the title compound. $^1$H NMR (400 MH$_z$, CD$_3$OD) δ8.61 (d, 1H), 8.08 (s, 1H), 7.95 (d, 1H), 7.60 (dd, 1H), 7.43 (d, 1H), 7.30–7.36 (m, 2H), 7.10 (s, 1H).

e) 2-[2-[3-(4-Chloro-3-(trifluoromethyl)phenyl]ureido]-4-(trifluoromethyl)phenoxy]-4,5-dichlorobenzenesulfonic acid, sodium salt A mixture of 2-[2-[3-(4-chloro-3-(trifluoromethyl)phenyl]ureido]-4-(trifluoromethyl)phenoxy]-4,5-dichlorobenzenesulfonic acid, ammonium salt (2.1 g, 3.28 mmol) and sodium bicarbonate (0.331 g, 3.94 mmol) in methanol (20 mL) and water (2 mL) were stirred under argon for 30 min. The solvents were evaporated, and the residue was flash chromatographed ($C_{18}$ reverse phase, MeOH/H$_2$O) to give the title compound after lyophilization. MS (ES) m/e 643.8 [M+H]$^+$.

EXAMPLE 2

2-[2-[3-[3,5-Bis(trifluoromethyl)phenyl]ureido]-4-trifluoromethylphenoxy]-5-(1,1 -dimethylpropyl)benzenesulfonic acid, sodium salt a) 2-(2-nitro-4-trifluoromethylphenoxy)-4-(1,1-dimethylpropyl)benzene A mixture of 4-(1,1-dimethylpropyl)phenol (821 mg, 0.005 mol), 4-bromo-3-nitrobenzotrifluoride (1.35g, 0.005 mol) potassium carbonate (1.38g, 0.010 mol) and cuprous oxide (143 mg, 0.001 mol) in dimethylformamide (25 ml) was stirred under argon at 150° C. for sixteen hours. The solvent was evaporated and the residue partitioned between ethyl acetate and water, the layers separated, dried over MgSO$_4$ and evaporated. The crude product flash chromatographed (silica gel, ethyl acetate/hexane) to give the title compound as a yellow oil. $^1$H NMR (250 MH$_z$, CDCl$_3$) ∂8.20 (d, 1H), 7.70 (dd, 1H), 7.45 (m, 2H), 7.05 (m, 3H), 1.65 (q, 3H), 1.30 (s, 6H), 0.65 (t, 2H).

b) 2-(2-Nitro-4-trifluoromethylphenoxy)-5-(1,1-dimethylpropyl)benzenesulfonic acid ammonium salt Fuming sulfuric acid (1 ml) was added to 2-(2-nitro-4-trifluoromethylphenoxy)-4-(1,1-dimethylpropyl)benzene (770 mg, 0.0022 mol) and stirred for forty-five minutes, quenched in ice, extracted with ethyl acetate, dried over $MgSO_4$ and evaporated. The residue was flash chromatographed (silica gel, methylene chloride/isopropanol/ammonium hydroxide) to give the title compound. $^1$H NMR (250 $MH_z$, $CD_3OD$) ∂7.95 (dd, 2H), 7.65 (dd, 1H), 7.45 (dd, 1H), 7.00 (d, 1H), 6.80 (d, 1H), 1.65 (q, 3H), 1.26 (s, 6H), 0.65 (t, 2H).

c) 2-(2-Amino-4-trifluoromethylphenoxy)-5-(1,1-dimethylpropyl)benzenesulfonic acid 2-(2-Nitro-4-trifluoromethylphenoxy)-5-(1,1-dimethylpropyl)benzenesulfonic acid, ammonium salt (620 mg) was mixed in ethyl acetate (50 ml) and palladium on carbon (202 mg) was added under argon. The mixture was hydrogenated in a Parr bottle at 55 psi for two hours. The sample was filtered to remove the catalyst, mixed with methanol and degassed for several hours to yield the title compound $^1$H NMR (250 $MH_z$, $CD_3OD$) ∂7.95 (d, 1H), 7.30 (dd, 1H), 7.05 (dd, 2H), 6.85 (dd, 1H), 6.75 (d, 1H), 1.65 (q, 3H), 1.25 (s, 6H), 0.65 (t, 2H).

d) 2-[2-[3-[3,5-Bis(trifluoromethyl)phenyl]ureido]-4-trifluoromethylphenoxy]-5-(1,1-dimethylpropyl)benzenesulfonic acid, ammonium salt 2-(2-Amino-4-trifluoromethylphenoxy)-5-(1,1-dimethylpropyl)benzenesulfonic acid (260 mg, 0.0006 mol) and 3,5-bis(trifluoromethyl)phenyl isocyanate (130.9 ml, 0.0005 mol) were mixed in pyridine (5 ml), under argon, for sixteen hours at room temperature. The solvent was evaporated and the residue flash chromatographed (silica gel, methylene chloride/isopropanol/ammonium hydroxide), dried and evaporated to give the title compound. $^1$H NMR (250 MHz, DMSO) ∂9.20 (s, 1H), 8.90 (s, 1H), 7.90 (s, 1H), 7.50 (s, 2H), 7.25 (d, 1H), 7.05 (s, 1H), 6.80–6.30 (m, 4H), 1.0 (q, 3H), 0.065 (s, 6H), 0.045 (d, 2H).

e) 2-[2-[3-[3,5-Bis(trifluoromethyl)phenyl]ureido]-4-trifluoromethylphenoxy]-5-(1,1 -dimethylpropyl)benzenesulfonic acid, sodium salt A mixture of 2-[2-[3-[3,5-bis(trifluoromethyl)phenyl]ureido]-4-trifluoromethylphenoxy]-5-(1,1-dimethylpropyl)benzenesulfonic acid, ammonium salt (254 mg, 0.0004 mol) and sodium bicarbonate (96 mg, 0.0011 mol) in methanol and water was stirred under argon for an hour. The solvents were evaporated and the residue was flash chromatographed ($C_{18}$ reverse phase, $MeOH/H_2O$) to give the title compound. MS (FAB) m/e 681 $[M+H]^+$.

EXAMPLE 3

2-[2-[3-(4-Chloro-3-trifluoromethylphenyl)ureido]-4-trifluoromethylphenoxy]-5-(1,1-dimethylpropyl)benezenesulfonic acid, sodium salt a) 2-(2-Nitro-4-trifluoromethylphenoxy)-4-(1,1-dimethylpropyl)benzene Following the procedure of Example 2(a) the title compound was made. $^1$H NMR (250 $MH_z$, $CDCl_3$) ∂8.20 (d, 1H), 7.70 (dd, 1H), 7.45 (m, 2H), 7.05 (m, 3H), 1.65 (q, 3H), 1.30 (s, 6H), 0.65 (t, 2H).

b) 2-(2-Nitro-4-trifluoromethylphenoxy)-5-(1,1-dimethylpropyl)benzenesulfonic acid, ammonium salt Following the procedure of Example 2(b) the title compound was made. $^1$H NMR (250 $MH_z$, $CD_3OD$) ∂7.95 (dd, 2H), 7.65 (dd, 1H), 7.45 (dd, 1H), 7.00 (d, 1H), 6.80 (d, 1H), 1.65 (q, 3H), 1.26 (s, 6H)), 0.65 (t, 2H).

c)2-(2-Amino-4-trifluoromethylphenoxy)-5-(1,1-dimethylpropyl)benzenesulfonic acid Following the procedure of Example 2(c) the title compound was made. $^1$H NMR (250 $MH^z$, $CD_3OD$) ∂7.95 (d, 1H), 7.30 (dd, 1H), 7.05 (dd, 2H), 6.85 (d, 1H), 6.75 (d, 1H), 1.65 (q, 3H), 1.25 (s, 6H), 0.65 (t, 2H).

d)2-[2-[3-(4-Chloro-3-trifluoromethylphenyl)ureido]-4-trifluoromethylphenoxy-5-(1,1-dimethylpropyl)benzenesulfonic acid, ammonium salt Following the procedure of Example 2(d) except substituting 4-chloro-3-trifluoromethylphenylisocyanate for 3,5-bis(trifluoromethyl)phenylisocyanate the title compound was made. $^1$H NMR (250 MHz, CD3OD) ∂8.55 (d, 1H), 7.95 (dd, 2H), 7.60 (dt, 1H), 7.49–7.20 (m, 4H), 6.89 (d, 1H), 1.60 (q, 3H), 1.20 (s, 6H), 0.65 (t, 2H).

e) 2-[2-[3-(4-Chloro-3-trifluoromethylphenyl)ureido-4-trifluoromethylphenoxy-5-(1,1-dimethylpropyl)benzenesulfonic acid, sodium salt Following the procedure of Example 2 (e) except substituting 2-[2-[3-(4-chloro-3 -trifluoromethylphenyl)ureido]-4-trifluoromethylphenoxy-5-(1,1-dimethylpropyl)benzenesulfonic acid, ammonium salt for 2-[2-[3-[3,5-bis(trifluoromethyl)phenyl]ureido]-4-trifluoromethylphenoxy]-5-(1,1-dimethylpropyl)benzenesulfonic acid, ammonium salt. MS (FAB) m/e 669 $[M+Na]^+$.

EXAMPLE 4

4,5-Dichloro-2-[3-(3,4-dichlorophenyl)ureido]-4-trifluoromethylphenyl)-thiobenzenesulfonic acid The title compound was purchased commercially. The title compound can also be made in an analogous manner to that of Example 1 above except using 3,4-dichlorothiophenol in place of 3,4-dichlorophenol and 3,4-dichlorophenylisocyanate in place of 4-chloro-3-trifluoro-methylphenylisocyanate.

EXAMPLE 5

4,5-Dichloro-2-[4-trifluoromethyl-2-(3-trifluoromethyl-4-chlorophenyl)ureido)phenyl)thio] benzenesulfonic acid The title compound was purchased commercially. The title compound can also be made in an analogous manner to that of Example 1 above except using 3,4-dichlorothiophenol in place of 3,4-dichlorophenol.

EXAMPLE 6

5-Chloro-2-[2-(3-(3,5-di-trifluoromethylphenyl)ureido)-4-trifluoromethylphenyl)thio]benzenesulfonic acid The title compound was purchased commercially. The title compound can also be made in an analogous manner to that of Example 1 above except using 4-chlorothiophenol in place of 3,4-dichlorophenol, and 3,5-bis(trifluoromethyl)phenyl isocyanate in place of 4-chloro-3-trifluoromethylphenyl isocyanate.

EXAMPLE 7

5-Chloro-2-[(4-chloro-2-((3-(5-chloro-3-trifluoromethylphenyl)ureido)phenyl)thio]benzenesulfonic acid The title compound was purchased commercially. The title compound can also be made in an analogous manner to that of Example 1 above except using 4-chlorothiophenol in place of 3,4-dichlorophenol, 2,5 dichloronitrobenzene in place of 4-chloro-3-nitrobenzotrifluoride, and 2-chloro-5-trifluoromethylphenylisocyanate in place of 4-chloro-3-trifluoromethylphenylisocyanate.

EXAMPLE 8

5-Chloro-2-[(4-chloro-2-[3-(2,4-dichlorophenyl)ureido)phenyl]thio]benzenesulfonic acid The title compound was purchased commercially. The title compound can also be made in an analogous manner to that of Example 1 above except using 4-chlorothiophenol in place of 3,4-dichlorophenol, 2,5 dichloronitrobenzene in place of 4-chloro-3-nitrobenzotrifluoride, and 2,4-dichlorophenylisocyanate in place of 4 -chloro-3-trifluoromethylphenyl isocyanate.

EXAMPLE 9

5-Chloro-2-[(4-chloro-2-(3-(4-chloro-3-trifluoromethylphenyl)ureido)phenyl)thio]benzenesulfonic acid The title compound was purchased commercially. The title compound can also be made in an analogous manner to that of Example 1 above except using 4-chlorothiophenol in place of 3,4-dichlorophenol and 2,5 dichloronitrobenzene in place of 4-chloro-3-nitrobenzotrifluoride.

EXAMPLE 10

5-Chloro-2-[(4-chloro-2-(3-(2,5-dichlorophenyl)ureido)phenyloxy]benzenesulfonic acid The title compound was purchased commercially. The title compound can also be made in an analogous manner to that of Example 1 above except using 4-chlorophenol in place of 3,4-dichlorophenol, 2,5-dichloronitrobenzene in place of 4-chloro-3-nitrobenzotrifluoride, and 2,5-dichlorophenylisocyanate in place of 4-chloro-3-trifluoromethylphenyl isocyanate.

EXAMPLE 11

2-[4-Chloro-2-[3-(6-chloro-α,α,α-trifluoro-3-tolyl)ureido)phenyloxy]-4,5-dichlorobenzenesulfonic acid The title compound was purchased commercially and is also referred to as 4,5 -Dichloro-2-[4-chloro-2-[[[[2-chloro-5-(trifluoromethyl)phenyl]-amino]carbonyl]amino]phenoxy]-benzenesulfonic acid)

The title compound can also be made in an analogous manner to that of Example 1 above except using 2,5 dichloronitrobenzene in place of 4-chloro-3-nitrobenzotrifluoride and 2-chloro-5-trifluoromethylphenyl isocyanate in place of 4-chloro-3-trifluoromethylphenyl isocyanate.

EXAMPLE 12

5-Chloro-2-[(4-chloro-2-[3-(4-chloro-α,α,α-trifluoro-3-tolyl)ureido)phenoxy]-4-toluenebenzenesulfonic acid The title compound was purchased commercially and is also referred to as 5-Chloro-2-[4-chloro-2-[[[[4-chloro-3-(trifluoromethyl)phenyl]amino]carbonyl]amino]-phenoxy]-4 -methylbenzenesulfonic acid.

The title compound can also be made in an analogous manner to that of Example 1 above except using 4-chloro-3-methylphenol in place of 3,4-dichlorophenol, and 2,5-dichloronitrobenzene in place of 4-chloro-3-nitrobenzotrifluoride.

EXAMPLE 13

5-Chloro-2-[(4-chloro-2-[3-(3,4-dichlorophenyl)ureido)phenyloxy]-4-toluenesulfonic acid The title compound was purchased commercially. The title compound can also be made in an analogous manner to that of Example 1 above except using 4-chloro-3-methylphenol in place of 3,4-dichlorophenol, 2,5-dichloronitrobenzene in place of 4-chloro-3-nitrobenzotrifluoride, and 3,4-dichlorophenyl isocyanate in place of 4-chloro-3-trifluoromethylphenyl isocyanate.

EXAMPLE 14

5-(1,1-Dimethylpropyl)-[2-[2-[3-(α,α,α-trifluoro-3tolyl)ureido]-α,α,α-trifluoro-4-olyloxy)benzene-sulfonic acid The title compound is also referred to as 5-Butyl-2-[4-(trifluoromethyl)-2-[[[3 -(trifluoromethyl)phenyl]amino]carbonyl]amino]phenoxy]-benzenesulfonic acid and was mande in an analagous manner to that of Example 2 and 3 above. MS (FAB) m/e 591˙[M+H]⁺.

The following compounds were all purchased commercially. The compounds, however, can also be made by one of skill in the art in an analogous manner to the Examples illustrated above.

EXAMPLE 15

2-[2-[3-(4-Chloro-2-tolyl)ureido]-4-chlorophenoxy]-3,5-dichlorobenzenesulfonic acid

EXAMPLE 16

5-Chloro-2-[4-chloro-2-[3-($\alpha,\alpha,\alpha,\alpha',\alpha',\alpha'$-hexafluoro-3,5-xylyl)ureido)phenoxy]-benzenesulfonic acid; also referred to as 2-[2-[[[[3,5-Bis(trifluoromethyl)-phenyl]amino]carbonyl]amino]-4-chlorophenoxy]-5-chlorobenzenesulfonic acid

EXAMPLE 17

4,5-Dichloro-2-[4-chloro-2-(3-(4-chloro-$\alpha,\alpha,\alpha$-trifluoro-3-tolyl)ureido)phenoxy]benzene-sulfonic acid; also referred to as 4,5-Dichloro-2-[4-chloro-2-[[[[4-chloro-3-(trifluoromethyl)phenyl]amino]carbonyl]amino]phenoxy]benzenesulfonic acid

EXAMPLE 18

5-Chloro-2-[4-chloro-2-(3-(6-chloro-$\alpha,\alpha,\alpha$-trifluoro-3-tolyl)ureido)phenoxy]benzene-sulfonic acid; also referred to as 5-Chloro-2-[4-chloro-2-[[[[2-chloro-5-(trifluoromethyl)phenyl]amino]carbonyl]amino]phenoxy]benzenesulfonic acid

EXAMPLE 19

5-Chloro-2-[4-chloro-2-(3-(4-chloro-$\alpha,\alpha,\alpha$-trifluoro-3-tolyl)ureido)phenoxy]benzene-sulfonic acid; also referred to as 5-Chloro-2-[4-chloro-2-[[[[4-chloro-3-(trifluoromethyl)phenyl]amino]carbonyl]amino]phenoxy]benzenesulfonic acid

EXAMPLE 20

5-Chloro-2-(4-chloro-2-(3,4-dichlorophenylaminocarbonylaminophenoxy)benzene sulfonic acid

EXAMPLE 21

5-Chloro-2-(4-chloro-2-(2,3-dichlorophenylaminocarbonylaminophenoxy)benzene sulfonic acid

EXAMPLE 22

5-Chloro-2-(4-chloro-2-(4-chlorophenylaminocarbonylaminophenoxy)benzene sulfonic acid

EXAMPLE 23

5-Chloro-2-(4-chloro-2-(3-trifluoromethylphenylaminocarbonylaminophenoxy)benzene sulfonic acid

EXAMPLE 24

5-Chloro-2-(4-chloro-2-(3-chloro-4-(4-chlorophenoxy)phenylaminocarbonylamino)-phenyoxybenzene sulfonic acid

EXAMPLE 25

5-Chloro-2-(4-chloro-2-(2-(3-chlorophenoxy)-5-trifluoromethylphenylaminocarbonylamino)phenyoxybenezene sulfonic acid

EXAMPLE 26

5-Chloro-2-[4-chloro-2-(5-chloro-2-(4-chlorophenoxy)phenylaminocarbonylamino)phenyoxy]benzene sulfonic acid.

METHODS OF TREATMENT

The compounds of Formula (I) and/or Formula (II) or pharmaceutically acceptable salts thereof can be used in the manufacture of a medicament for the prophylactic or therapeutic treatment of an inflammatory disease state in a mammal, preferably a human.

Inhibition of $PLA_2$ and/or CoA-IT and the simultaneous reduction of PAF, free arachidonic acid and eicosanoid release: from inflammatory cells according to this invention is of therapeutic benefit in a broad range of diseases or disorders. The invention herein is therefore useful to treat such disease states both in humans and in other mammals.

Inhibition of CoA-IT and 14 kDa $PLA_2$ by the compounds of Formula (I) and/or Formula (II) is an effective means for simultaneously reducing PAF, free arachidonic acid and eicosanoids produced in inflammatory cells. The therapeutic utility of blocking lipid mediator generation has been recognized for many years. For example, inhibitors of cyclooxygenase, such as aspirin, indomethacin, acetaminophen and ibuprofen, have demonstrated broad therapeutic utilities. CoA-IT inhibitors inhibit cyclooxygenase products. Another class of inhibitors which are used in a broad range of inflammatory disorders are the corticosteroids. Corticosteroids act in a variety of ways, e.g. to induce inflammatory cells to produce proteins which inhibit free arachidonic acid release or to down regulate $PLA_2$ mRNA formation. Both 14 kDa $PLA_2$ inhibitors and CoA-IT inhibitors block the release of free arachidonic acid. Inhibitors of 5-lipoxygenase block the production of leukotrienes and leukotriene antagonists prevent the bioactions of leukotrienes. Recent studies indicate that both will have broad therapeutic utilities. Both 14 kDa $PLA_2$ inhibitors and CoA-IT inhibitors block the production of leukotrienes. Inhibitors of phospholipase $A_2$ block the release of free arachidonic acid and the formation of lyso PAF (the immediate precursor of PAF). $PLA_2$ inhibitors are recognized to have broad therapeutic utilities. It does not, however, follow that the disease states noted above must in fact be caused by altered CoA-IT or $PLA_2$ activity. Thus, the disease state itself may not be directly mediated by CoA-IT or $PLA_2$ activity. It only follows that CoA-IT or $PLA_2$ activity is required for the continued expression of symptoms of the disease state and that CoA-IT or $PLA_2$ inhibitors will be beneficial against the symptoms of these disease states.

Recognition that 14 kDa $PLA_2$ and/or CoA-IT inhibitors reduce PAF production has a number of therapeutic implications. PAF itself has been implicated as being involved in a number of medical conditions. Thus in circulatory shock, which is characterised by systemic hypotension, pulmonary hypertension and increased lung vascular permeability, the symptoms can be mimicked by infusion of PAF. This coupled with evidence showing that circulating PAF levels are increased by endotoxin infusion indicate that PAF is a prime mediator in certain forms of shock.

Intravenous infusion of PAF at doses of 20–200 pmol kg$<-1>$min$<-1>$into rats has been reported to result in the formation of extensive haemorrhagic erosions in the gastric mucosa. Thus PAF is the most potent gastric ulcerogen yet described whose endogenous release may underlie or contribute to certain forms of gastric ulceration. Psoriasis is an inflammatory and proliferative disease characterised by skin lesions. PAF is proinflammatory and has been isolated from lesioned scale of psoriatic patients indicating PAF has a role is the disease of psoriasis. And finally, increasing evidence supports a potential patho-physiological role for PAF in cardiovascular disease. Thus recent studies in angina patients show PAF is released during atrial pacing. Intracoronary injection of PAF in pigs induces a prolonged decrease in coronary flow and, in guinea pig hearts, it induces regional shunting and ischaemia. In addition PAF has been shown to initiate thrombus formation in a mesenteric artery preparation, both when administered exogenously and when released endogenously. More recently PAF has been shown to play a role in brain ischaemia induced in animal models of stroke. Thus the compounds of the invention, by virtue of their ability to antagonise either CoA-IT and/or $PLA_2$, thus block the production of PAF, free arachidonic acid and its metabolites, are likely to be of value in the treatment of any of the above conditions.

The action of a $PLA_2$ inhibitor can be distinguished from the activity of a CoA-IT inhibitor based on their specific actions on their respective enzymes and by their different effects in cellular assays. For example only CoAL-IT inhibitors have the ability to interfere with the mobilization of radiolabelled arachidonic acid to move from the alkyl-PC pool to the alkenyl PE pool. Selective inhibitors of 14 kDa $PLA_2$ are without an effect in this assay (assay E). Alternatively, CoA-IT inhibitors will inhibit both $LTC_4$ and $PGE_2$ release from activated monocytes while selective $PLA_2$ inhibitors inhibit LTC4 release but spare prostanoid formation or production (assay F).

Disease states which could benefit from the inhibition of lipid mediator production include, but are not limited to, adult respiratory distress syndrome, asthma, arthritis, reperfusion injury, endotoxic shock, inflammatory bowel disease, allergic rhinitis and various inflammatory skin disorders. Each of these disorders is mediated in some part by lipid mediators of inflammation. Compounds which inhibit CoA-IT, by virtue of their ability to block the generation of lipid mediators of inflammation, are of value in the treatment of any of these conditions. Similarly compounds which inhibit $PLA_2$, by virtue of their ability to block the generation of lipid mediators of inflammation stemming from activation and/or release of this enzyme are of value in the treatment of these conditions. In particular, an inhibitor of CoAIT, for instance would offer an advantage over the classical NSAIDs which affect only prostanoid production (and not PAF biosynthesis) thereby inhibiting both the acute and cell-mediated "chronic" inflammatory processes. Further an advantage of the $PLA_2$ inhibitor would be their affect on human monocyte leukotrienes and PAF formation, while immunosuppressive prostanoids, such as $PGE_2$, are spared.

Treatment of disease states caused by these lipid inflammatory mediators i.e., arachidonate, eicosanoids and PAF, include certain cardiovascular disorders such as but not limited to, myocardial infarction, stroke, circulatory shock, or hypotension, ischemia, reperfusion injury, inflammatory diseases such as, but not limited to, arthritis, inflammatory bowel disease, Crohn's disease, or ulcerative colitis, respiratory disease such as but not limited to, asthma, or adult respiratory distress syndrome, analphylaxis, shock such as but not limited to endotoxic shock, topical disesases, such as but not limited to actinic keratosis; psoriasis, or contact dermatitis, or pyresis.

In order to use a compound of formula (I) or (II) or a pharmaceutically acceptable salt thereof in therapy, it will normally be formulated into a pharmaceutical composition in accordance with standard pharmaceutical practice. This invention, therefore, also relates to a pharmaceutical composition comprising an effective, non-toxic mount of a compound of formula (I) or (ID and a pharmaceutically acceptable cattier or diluent.

Compounds of formula (I) or (II), pharmaceutically acceptable salts thereof and pharmaceutical compositions incorporating such may conveniently be administered by any of the routes conventionally used for drug administration, for instance, orally, topically, parenterally or by inhalation. The compounds of formula (I) or (II) may be administered in conventional dosage forms prepared by combining a compound of formula (I) or (II) with standard pharmaceutical carriers according to conventional procedures. Such pharmaceutically acceptable carriers or diluents and methods of making are well known to those of skill in the art, and reference can be found in such texts as Remington's Pharmaceutical Sciences, 18th Ed., Alfonso R. Genarao, Ed., 1990, Mack Publishing Co. and the Handbook of Pharmaceutical Excipents, APhA Publications, 1986.

The compounds of formula (I) or (II) may also be administered in conventional dosages in combination with known second therapeutically active compounds, such as steroids or NSAID's for instance. These procedures may involve mixing, granulating and compressing or dissolving the ingredients as appropriate to the desired preparation. It will be appreciated that the form and character of the pharmaceutically acceptable carrier or diluent is dictated by the amount of active ingredient with which it is to be combined, the route of administration and other well-known variables. The carrier(s) must be "acceptable" in the sense of being compatible with the other ingredients of the formulation and not deleterious to the recipient thereof.

The pharmaceutical carder employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time delay material well known to the art, such as glyceryl mono-stearate or glyceryl distearate alone or with a wax.

A wide variety of pharmaceutical forms can be employed. Thus, if a solid carrier is used, the preparation can be tableted, placed in a hard gelatin capsule in powder or pellet form or in the form of a troche or lozenge. The amount of solid carrier will vary widely but preferably will be from about 25 mg. to about 1 g. When a liquid carrier is used, the preparation will be in the form of a syrup, emulsion, soft gelatin capsule, sterile injectable liquid such as an ampule or nonaqueous liquid suspension.

Compounds of formula (I) or (II) may be administered topically, that is by non-systemic administration. This includes the application of a compound of formula (I) or (II) externally to the epidermis or the buccal cavity and the instigation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as liniments, lotions, creams, ointments or pastes, and drops suitable for administration to the eye, ear or nose. The active ingredient may comprise, for topical administration, from 0.001% to 10% w/w, for instance from 1% to 2% by weight of the formulation. It may however comprise as much as 10% w/w but preferably will comprise less than 5% w/w, more preferably from 0.1% to 1% w/w of the formulation.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy base. The base may comprise hydrocarbons such as hard, soft or liquid paraffin, glycerol, beeswax, a metallic soap; a mucilage; an off of natural origin such as almond, corn, arachis, castor or olive oil; wool fat or its derivatives or a fatty acid such as steric or oleic acid together with an alcohol such as propylene glycol or a macrogel. The formulation may incorporate any suitable surface active agent such as an anionic, cationic or non-ionic surfactant such as a sorbitan esteror a polyoxyethylene derivative thereof. Suspending agents such as natural gums, cellulose derivatives or inorganic materials such as silicaceous silicas, and other ingredients such as lanolin, may also be included.

Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified by filtration, transferred to a suitable container which is then sealed and sterilized by autoclaving or maintaining at 98°–100° C. for hag an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Each dosage unit for oral administration contains preferably from 1 to 250 mg (and for parenteral administration contains preferably from 0.1 to 25 mg) of a compound of the structure (I) or a pharmaceutically acceptable salt thereof calculated as the free base.

The pharmaceutically acceptable compounds of the invention will normally be administered to a subject in a dally dosage regimen. For an adult patient this may be, for example, an oral dose of between 1 mg and 500 mg, preferably between 1 mg and 250 mg, or an intravenous, subcutaneous, or intramuscular dose of between 0.1 mg and 100 mg, preferably between 0.1 mg and 25 mg, of the compound of the Formula (I)/(II) or a pharmaceutically acceptable salt thereof calculated as the free base, the compound being administered from 1 to 4 times per day.

The choice of form for administration, as well as effective dosages, will vary depending, inter alia, on the condition being treated. The choice of mode of administration and dosage is within the skill of the art.

BIOLOGICAL METHODS

To determine activity of the compounds of Formula (I) and (II) various cellular assays can be used to determine in vitro activity. Additionally, various classical in vivo acute inflammatory models which have some aspect of their etiology to elevated eicosanoid levels can be employed, such as the paw edema model, mouse zymosan peritonitis, reverse Arthus pleurisy or various skin inflammation assays which are described in Lewis et al., Experimental Models of inflammation, in the *Handbook of Inflammation*, Vol. 5, Bonta Ed., Elsevier Science Publishers, New York (1985) whose disclosure is herein incorporated by reference. The TPA induced ear edema model (mouse) as well as the carrageenan paw edema model in the rat are described herein as well. These classical models of inflammation will reflect the drug's ability to alter an inflammatory response but cannot address the specificity of drug action. These models have been traditionally designed as non steriod antiinflammatory drug sensitive pharmacological screens and it is important to utilize models which can differentiate PLA2 and CoA-IT inhibitors from NSAIDS.

Cell-free and Cellular Assessment of Inhibitors

Described herein are several in vitro assays both for CoA-IT and $PLA_2$ enzyme activities. The first employs purified recombinant enzyme or a broken cell assay, assay (a or b, respectively) described below. Alternatively, evaluation of inhibitors can occur in intact cells such as described in the assay, assay (c and d) below. CoA-IT activity can exclusively be measured, and differentiated from $PLA_2$ inhibition, in intact cells by following the movement of a pulse of [$^3$H] arachidonate as it moves into the 1-alkyl and 1-alkenyl phospholipids in inflammatory cells (assay e). It should be noted for the purposes herein that assays c, d, & f can both be used for $PLA_2$ and CoA-IT inhibition determination.

Inflammatory Responses in vivo

The ability of compounds that inhibit CoA-IT and/or $PLA_2$ to affect in vivo inflammatory responses may be assessed. Inflammatory responses are induced in the mouse ear by the topical application of a pro-inflammatory agent, such as 12-0-tetradecanoylphorbol 13-acetate (assay g). This produces an edematous response, as measured by increases in ear thickness, as well as increased inflammatory cellular infiltrate, as measured by increases in myeloperoxidase activity (as described in the methods). To further validate the mechanism of action inflammation induced by the direct administration of arachidonic acid can be used. In this case, compounds altering arachidonic acid mobilization or liberation should be without effect.

IN VITRO ASSAYS

Assay (a): Phospholipase $A_2$ assay:

Phospholipase $A_2$ activity of rh Type II-14 KDaPLA$_2$ or $PLA_2$ semi-purified from human Synovial joint fluid was measured by the acylhydrolysis of high specific activity (NEN)[$^3$H]-AA-*E. coli* (0.5 mCi/5 nmol PL Pi) as previously described in Marshall et al., J. Rheumatology, 18:1, pp59–65 (1991). High specific activity [$^3$H]AA-*E. coli* had up to 95% of the label incorporated into phospholipid which was localized almost exclusively in the sn-2 position, as demonstrated by purified 14 kDa PLA$_2$ or low molecular weight PLA$_2$ acylhydrolysis and separation of products by thin layer chromatography (TLC) (data not shown). [Predominately used herein was rh Type II 14 kDa PLA2, or alternatively bovine pancreatic PLA$_2$ was also be used]. The reaction mixture (50 or 100 ml total volume) contained 25 mM HEPES, pH 7.4, 150 mM NaCl, 5 mM CaCl$_2$ and [$^3$H]-AA-*E. coli* (low specific activity; 5–8 nmol PL Pi per assay). Assays were incubated for a time predetermined to be on the linear portion of a time versus hydrolysis plot (10 min). Experiments were conducted with final % hydrolysis values ranging from 2% (400–1000 dpm) to 10% (2000–5000 dpm) acylhydrolysis after blank correction.

Reactions were terminated by the addition of 1.0 mL tetrahydrofuran (THF). The whole sample was placed over aminopropyl solid phase silica columns and eluted with THF:acetic acid (49:1 ) exclusively separating free fatty acids with greater than 95% recovery. Radiolabel in this eluate was quantitated by liquid scintillation counting. Results were expressed as % of fatty acid hydrolyzed ([sample dpms−non-specific (blank) dpms/total dpms]×100) or specific activity which was calculated from hydrolysis values found in the linear portion of time versus % hydrolysis plots (pmol free fatty acid hydrolyzed/mg/min). Non-specific activity was always less than 1% of the total counts added.

Protein determination

All protein concentrations were determined by Bradford protein analysis kits (Biorad, Richmond, Calif.).

Results:

The following representative compounds of Formula (I) and (II) below demonstrated positive $PLA_2$ inhibition in the above noted method. While these compounds generally tested positive at 50 μm levels, several were also tested for positive inhibitory activity at up to 500 μM levels. Such compounds include:

5-Chloro-2-[(4-chloro-2-(3-(2,5-dichlorophenyl)ureido)phenyloxy]benzenesulfonic acid;

2-[4-Chloro-2-[3-(6-chloro-α,α,α-trifluoro-3-tolyl)ureido)phenyloxy]-4,5 -dichlorobenzenesulfonic acid;

5-Chloro-2-[(4-chloro-2-[3-(3,4-dichlorophenyl)ureido)phenyloxy]-4-toluenesulfonic acid;

2-[2-[3-(4-Chloro-2-tolyl)ureido]-4-chlorophenoxy]-3,5-dichlorobenzenesulfonic acid;

2-[2-[3-(4-Chloro-3-trifluoromethylphenyl)ureido]-4-trifluoromethylphenoxy]-4,5 -dichlorobenzene sulfonic acid;

5-Chloro-2-[4-chloro-2-[3-(α,α,α,α',α',α'-hexafluoro- 3,5-xylyl)ureido)phenoxy]-benzenesulfonic acid;

5-(1,1-Dimethylpropyl)-[2-[2-[3-(α,α,α-trifluoro-3-tolyl)ureido] -α,α,α-trifluoro-4-tolyloxy)benzenesulfonic acid;

2-[2-[3-(4-Chloro-3-trifluoromethylphenyl)ureido]-4-trifluoromethylphenoxy]-5-(1,1-dimethethylpropyl)benzenesulfonic acid;

2-[[2-[3-(α,α,α,α',α',α'-hexafluoro-3,5-xylyl)ureido] -α,α, α-trifluroro-4-tolyloxy]-5-(1,1-dimethylpropyl)benzenesulfonic acid;

5-Chloro-2-[4-chloro-2-(3-(4-chloro-α,α,α-trifluoro-3-tyl)ureido)phenoxy] benzenesulfonic acid;

5-Chloro-2-(4-chloro-2-(3,4-dichlorophenylaminocarbonylaminophenoxy)benzene sulfonic acid;

5-Chloro-2-(4-chloro-2-(2,3-dichlorophenylaminocarbonylaminophenoxy)benzene sulfonic acid;

5-Chloro-2-(4-chloro-2-(4-chlorophenylaminocarbonylaminophenoxy)benzene sulfonic acid;

5-Chloro-2-(4-chloro-2-(3-trifluoromethylphenylaminocarbonylaminophenoxy)benzene sulfonic acid;

5-Chloro-2-[4-chloro-2-(2-chloro-5-trifluoromethylphenylamino)carbonylamino]phenoxybenzene sulfonic acid;

5-Chloro-2-(4-chloro-2-(3-chloro-4-(4-chlorophenoxy)-phenylaminocarbonylamino)phenyoxybenzene sulfonic acid;

5-Chloro-2-(4-chloro-2-(2-(3-chlorophenoxy)-5 -trifluoromethylphenylaminocarbonylamino)phenyoxybenzene sulfonic acid; and 5-Chloro-2-[4-chloro-2-(5-chloro-2-(4-chlorophenoxy)phenylaminocarbonylamino)phenyoxy]benzene sulfonic acid.

Assay (b): CoA-IT Activity

The following is a method to measure CoA-IT activity and the effects of compounds on CoA-IT activity. The assay is based upon mixing cellular material containing CoA-IT activity with a stable lyso phospholipid such as 1-alkyl-2-acyl-GPC and measuring the production of phospholipid product such as 1-alkyl-2-acyl-GPC occurring in the absence of added CoA or CoA-fatty acids.

Cell Preparation

Any inflammatory cell that contains high levels of CoA-IT activity can be used, such as neutrophils, macrophages or cell lines such as U937 cells. U937 cells were obtained from American Type Culture Collection and grown in RPMI-1640 media (Gibco, Grand Island, N.Y.) supplemented with 10% fetal bovine serum (Hyclone, Logan, Utah) at 37° C., 5% $CO_2$. Cells were grown without differentiation (basal state) by any agent, such as dimethyl sulfoxide. As used herein, "inflammatory cells" include, but are not limited to neutrophils, macrophages, monocytes, lymphocytes, eosinophils, basophils, and mast cells.

Microsomal preparation

Microsomes were prepared using standard techniques. In this case, cells were washed with a buffer of 250 mM sucrose, 10 mM Tris, 1 mM EGTA, 1 mM $MgCl_2$, pH 7.4 and ruptured by $N_2$ cavitation (750 psi, 10 minutes). The ruptured cells were centrifuged 1000×g, 5 minutes. The resulting supernatant was centrifuged at 20,000×g,−20 minutes. Microsomes were prepared from this supernatant by centrifugation at 100,000×g, 60 minutes. The resulting pellet was washed once with assay buffer (150 mM NaCl, 10 mM $Na_2KPO_4$, 1 mM EGTA, pH 7.4), recentrifuged and the pellet resuspended in assay buffer (4–20 mg protein/ml) and was stored at −80° C. until assayed.

CoA-IT activity

CoA-IT activity was measured in 1.5 ml centrifuge tubes in a total volume of 100 ul. Microsomes were diluted in assay buffer to the desired protein concentration (6–20 ug/tube). The reaction was initiated by addition of [3H]1-alkyl-2-lyso-sn-glycero-3-phosphocholine (GPC) (~0.1 uCi/tube) and 1 μM final cold 1-alkyl-2-lyso-GPC in assay buffer with 0.25 mg/ml fatty acid-poor bovine serumalbumin (BSA) (Calbiochem, La Jolla, Calif.). [$^3$H]1-alkyl-2-lyso-GPC, approximately 50 Ci/mmol, was from NEN-Dupont (Boston, Mass.) and cold 1-alkyl-2-lyso-GPC was from Biomol (Plymouth Meeting, Penn.). Microsomes were pretreated with desired agents for the desired time (10 minutes) before the addition of [$^3$H]1-alkyl-2-lyso-GPC. The reaction was run for the desired time (10 minutes) at 37° C. The reaction was stopped and the lipids extracted by addition of 100 ul of chloroform:methanol (1:2, v/v) followed by 100 ul of chloroform and 100 ul of 1M KCI. The samples were vortexed and centrifuged at high speed in a microfuge for 2–3 minutes. An aliquot of the chloroform-extracted materials were separated, usually by TLC in chloroform/methanol/acetic acid/water (50:25:8:4, v/V), visualized by radioscanning (Bioscan) and the product, [$^3$H]1-alkyl-2-acyl-GPC, was scraped and quantified by liquid scintillation spectroscopy. With this TLC system, the synthetic standards of 1-alkyl-2-lyso-GPC and 1-alkyl-2-acyl-GPC were well separated, with Rf values of approximately 0.25 and 0.65, respectively. Other methods can be used to separate substrate from product, including but not limited to column chromatography, affinity chromatography and post reaction derivitization.

Protein concentration were assessed using the protein assay reagents from Bio-Rad (Richmond, Calif.).

Result

A variety of compounds have been tested in this assay to determine its selectivity and inability to detect trivial, non-selective inhibitors. Inhibitors of 5-lipoxygenase (5-LO) and cyclooxygenase (CO), such as indomethicin, naproxen, 6-(4'-Fluorophenyl)-5-(4-pyridyl)-2,3-dihydroimidzo-[2,1-b]thiazole and 6-(4'-Fluorophenyl)-5-(4-pyridyl)2,3-dihydroimidzo-[ 2,1-b]thiazole-dioxide had no effect in CoA-IT activity at concentrations up to 100 μM. The anti-oxidant BHT also has no effect at concentrations up to 100 μM. Compounds which complex with phospholipids and inhibit $PLA_2$ activity, such as quinacrine and aristolochic acid have no effect on CoA-IT activity at concentrations up to 500 μM. Doxepine, a compound reported to inhibit PAF release did not inhibit CoA-IT at concentrations up to 100 μM. Sodium diclofenac, reported to decrease leukotriene production by altering arachidonic acid metabolism, had no effect on CoA-IT activity at concentrations up to 500 μM. These results show that the assay for CoA-IT activity is sensitive and selective.

Representative compounds of Formula (I) and (II) which inhibit CoA-IT activity in the microsomal CoA-IT assay above [generally at 50 μM or less] are:

4,5-Dichloro-2-[4-trifluoromethyl-2-(3-trifluoromethyl-4-chlorophenyl)ureido)phenyl]thio] benzenesulfonic acid;

2-[2-[3-(4-Chloro-3-(trifluoromethyl)phenyl]ureido]-4-(trifluoromethyl)phenoxy]-4,5-dichlorobenzenesulfonic acid, sodium salt;

2-[2-[3-[3,5-Bis(trifluoromethyl)phenyl]ureido]-4-trifluoromethylphenoxy]-5-(1,1-dimethylpropyl)benzenesulfonic acid, sodium salt;

5-Chloro-2-[(4-chloro-2-[3-(4-chloro-α,α,α-trifluoro-3-tolyl)ureido)phenoxy] -4-toluene-benzenesulfonic acid;

4,5-Dichloro-2-[4-chloro-2-(3-(4-chloro-α,α,α-trifluoro-3-tolyl)ureido)phenoxy]benzene-sulfonic acid; and 5-Chloro-2-(4-chloro-2-(3,4-dichlorophenylaminocarbonylaminophenoxy)benzene sulfonic acid.

Assay (c): Arachidonic Acid Release Assay

Preparation of human neutrophils

Human neutrophils are obtained in the laboratory using three different methods. One method uses leukophoresis packs from normal humans and neutrophils are isolated using the histopaque-1077 technique. The blood is centrifuged at 300×g for 10 minutes. The cell pellets are resuspended in PBS composed of 137 mM NaCl, 8.8 mM Na2HPO4, 1.5 mM KH2PO4, 2.7 mM KCl (Dulbecco's Gibco Laboratories, Long Island, N.Y.) and layered over histopaque-1077 (Sigma, St. Louis, Mo.). The pellets are collected after centrifugation (300×g for 30 minutes) and washed once in PBS. The cell pellets are exposed briefly to deionized water to lyse any erythrocytes. The remaining cells are collected by centrifugation, suspended in PBS, counted and identified after cytospinning and staining. The final leukocyte preparation will be of greater than 95% purity and viability.

The second method isolates human neutrophils from fresh heparinized normal blood using the Histopaque-1077 technique. The blood is layered over Histopaque-1077 (Sigma, St. Louis Mo.) and centrifuged at 400×g for 30 minutes. The cell pellets are resuspended in 35 ml of PBS and 12 ml of 6% Dextran, followed by Dextran sedimentation at room temperature for 45 minutes. The upper layer is collected and further centrifugated for 10 minutes at 1000 rpm. The cell pellets are exposed briefly to deionized water to lyse erythrocytes. The remaining cells are collected by centrifugation, suspended in PBS, counted and identified after cytospinning and staining. The final leukocyte preparation will be of greater than 95% purity and viability.

The third method isolates human neutrophils from freshly drawn heparinized normal blood using the Percoll technique. The, blood is first treated with 6% Dextran at room temperature for a 1 hour sedmination. The upper layers of plasma are collected and centrifuged at 400×g for 10 minutes. The cell pellets are resuspended in Percoll 1.070 g/ml supplemented with 5% fetal bovine serum and layered on discontinuous gradients (1.080, 1.085, 1.090,1.095 g/ml) followed by centrifugation at 400×g for 45 minutes. The neutrophils are collected from interfaces of 1;080 and 1.085 and the 1.085 and 1.090 Percoll densities, followed by a centrifugation at 400×g for 45 minutes. The neutrophils are suspended in PBS, counted and identified after cytospinning and staining. The final leukocyte preparation will be of greater than 95% purity and viability.

There should be no difference noted in the response of the neutrophils nor in the effects of test compounds in neutrophils isolated by the three different techniques.

Treatment of human neutrophils

Neutrophils are suspended in PBS with 1 mM $Ca^{2+}$ and 1.1 mM $Mg^{2+}$ at concentrations of 5 to 20×106 cells per ml. Cells are added to test tubes and treated with the desired compounds for 5 to 10 minutes, then challenged with calcium ionophere A23187, 2 μM, or vehicle control, PBS containing 0.25–1 mg/ml BSA. After 5 to 20 minutes, the reactions are terminated by addition of an equal volume of chloroform:methanol (1:2, v/v) to the samples. [$^2H_8$]Arachidonic acid (50, 100 or 200 ng) is added as an internal standard and the lipids ware extracted by addition of equal volumes of chloroform and distilled water. The samples are vortexed and centrifuged at high speed and the chloroform layer removed to a clean tube.

Assay for free arachidonic acid

The chloroform extract for each sample is evaporated to dryness and the material resuspended in hexane. The hexane is passed through a Silica solid phase column (500 mg), washed 2× with hexane and a fatty acid enriched fraction eluted with hexane:ethyl ether (1:1, v/v). Solvents are removed from the samples under a stream of nitrogen then the samples are converted to pentafluorobenzyl esters using pentafluorobenzyl bromide and diisopropylethylamine in acetonitrile. Solvents are removed and samples are suspended in hexane. GC/MS analysis is performed on a suitable instrument, such as a Finnigan MAT TSQ 700 GC/MS/MS/DS (San Jose, Calif.) operated as a single stage quadruple system or a Hewlett-Packard 5890 with a 5989A M5 system.

The peaks corresponding to arachidonic acid and [$^2H_8$] Arachidonic acid are identified and the areas of those peaks compared and the released arachidonic acid calculated as ng of arachidonic acid for each sample.

Protein concentrations are assessed using the protein assay reagents from Bio-Rad (Richmond, Calif.).

A representative compound herein which demonstrated positive activity, i.e., inhibition of arachidonic acid release in this assay are:

2-[2-[3-(4-Chloro-3-trifluromethylphenyl)ureido]-4-trifluoromethylphenoxy] -4,5-dichlorobenzene sulfonic acid; and 2-[2-[[[[3,5-Bis(trifluoromethyl)phenyl]amino]carbonyl]amino]-4-(trifluoromethyl)phenoxy]-5-(1,1-dimethylpropyl)benzenesulfonic acid;

Assay (d): Assay for Production of Platelet-Activating Factor (PAF)

Preparation of human neutrophils:

Blood is obtained from normal humans and neutrophils are isolated as described for the arachidonic acid release assay, above. The final leukocyte preparation should be of greater than 95% purity and viability.

Treatment of human neutrophils

Neutrophils are suspended in PBS at concentrations of 5 to 20×10⁶ cells per ml. Cells are added to test tubes and treated with the desired compounds for 5 to 10 minutes, then challenged with calcium ionophore A23187, 2 µM and 20–30 µCi of [3H]acetic acid (NEN-Dupont, Boston, Mass.), or the vehicle of PBS with 0.25–1 mg/ml. After 5 to 20 minutes, the reactions are terminated by addition of an equal volume of chloroform:methanol (1:2, v/v) to the samples and the lipids are extracted by addition of equal volumes of chloroform and distilled water. The samples are vortexed and centrifuged at high speed and the chloroform layer removed to a clean tube.

Assay for PAF

The chloroform from each tube is evaporated to dryness and the material suspended in a small volume of chloroform or chloroform:methanol (25–100 µl) and the total material spotted on a Silica TLC plate. The plates are developed in chloroform/methanol/acetic acid/water (50:25:8:4, v/v) visualized by radioscanning (Bioscan) and the product, [³H]PAF, is scraped and quantified by liquid scintillation spectroscopy. With this TLC system, the Rf value for a synthetic standard of PAF is approximately 0.33.

A representative compound herein which demonstrated positive activity, i.e., inhibition of PAF production, in this assay is:

2-[2-[3-(4-Chloro-3-trifluoromethylphenyl)ureido]-4-trifluoromethylphenoxy]-4,5-dichlorobenzene sulfonic acid; and Assay (e): Methods for the evaluation of CoA-IT inhibitors on mobilization of labeled arachidonic acid in intact cells Measurement of the effect of CoA-IT inhibitors on the transfer of [³H]arachidonate into 1-ether phospholipids in non-stimulated inflammatory cells can be accomplished by general application of the following specific method. Human neutrophils were isolated and resuspended (5×10⁷/ml) in Hanks Balanced Salt Solution (HBSS; Gibco). [5,6,8,9,11,12,14,15-³H]-Arachidonic acid (100 Ci/mmol; New England Nuclear) complexed to 200 µl HBSS containing 0.25 mg/ml HSA was added to the cell suspension (1 µCi/ml). The cells were incubated with gentle shaking at 37° C. for 5 min. The reaction was terminated by the addition of 40 ml ice-cold HBSS containing HSA (0.25 mg/ml). The cells were then removed from the supernatant fluid by centrifugation (225 g, 8 min). Unincorporated [³H]-arachidonic acid was completely removed by two more washes of HBSS containing 0.25 mg/ml HSA. The neutrophils were resuspended in fresh buffer, exposed to various concentrations of a CoA-IT inhibitor or its vehicle and incubated without stimulation for 2 hrs. At that time, the tubes containing the cells and buffer were extracted (Bligh & Dyer [Can. J. Biochem. Physiol. (1959) 37, 911–917]) and the phospholipid classes separated and collected by normal phase HPLC, using a Ultrasphere Silica column (4.6 mm×250 mm; Rainin) eluted with hexane/2-propanol/ethanol/phosphate buffer (pH 7.4)/acetic acid (490:367:100:30:0.6 v/v) for 5 min at a flow rate of 1 ml/min. The amount of phosphate buffer in the eluting solvent was increased to 5 % over 10 rain and this solvent composition was maintained until all the phospholipid classes had eluted from the column (30–40 min) (Chilton, F. H. [Methods Enzymol. (1990)187, 157–166]). The phospholipids were converted into diradylglycerols by addition of phospholipase C, 20 units-40 units of *Bacillus cereus* phospholipase C (Sigma Type XIII) in 100 mM Tris HCl buffer (pH 7.4) for 2.5–6 hr, then convened into 1,2-diradyl-3-acetylglycerols by incubation with acetic anhydride and pyridine (Chilton, F. H. [Methods Enzymol. (1990)187, 157–166]). The phospholipid subclasses were separated by TLC in benzene/hexane/ethyl ether (50:45:4, v/v), located by image analysis (Bioscan) and the amount of radioactivity in each class was determined by zonal scraping and liquid scintillation counting.

A representative compound herein which demonstrated positive activity, i.e., blocking the movement of arachidonic acid into 1-ether phospholipids in this assay is:

2-[2-[3-(4-Chloro-3-trifluoromethylphenyl)ureido]-4-trifluoromethylphenoxy]-4,5-dichlorobenzene sulfonic acid; and The following is the method for assessing the ability of a compound to alter arachidonate content of cellular phospholipids, which can be generalized for any desired cell. Specifically, mouse bone marrow-derived mast cells are removed from culture and provided with exogenous [³H] arachidonic acid for 30 minutes. The labeled arachidonic acid which had not been incorporated into the cells is then removed by washing the cells 2 times with an albumin-containing buffer. At that point, the cells are treated with various concentrations of CoA-IT inhibitors and then placed back in culture for 24–48 hours. The phospholipids are extracted by the method of Bligh and Dyer [Can. J. Biochem. Physiol. (1959) 37, 911–917] and phospholipids separated by normal phase HPLC by the method of Chilton [Methods Enzymol. (1990)187, 157–166]. The radioactive and mole quantities of arachidonate in complex lipids are determined. At this point, cellular lipid extracts are treated with KOH (0.5M) to remove fatty acids from complex lipids (phospholipids) and the quantities of arachidonate in these extracts can then be determined by various methods, including gas chromatography and mass spectrometry (Chilton [Methods Enzymol. (1990)187, 157–166]).

A representative compound herein which demonstrated positive activity, i.e., decreasing the arachidonic content, in this assay is:

2-[2-[3-(4-Chloro-3-trifluoromethylphenyl)ureido]-4-trifluoromethylphenoxy]-4,5-dichlorobenzene sulfonic acid; and Assay (f) for measurement of stimulated eicosanoid release by human monocytes.

Human Monocyte Isolation. Leukocyte-rich leukopaks obtained from Biological Specialties (Lansdale, Pa.) were collected from male volunteers who were not taking anti-inflammatory drugs. Leukopaks were centrifuged (90×g for 15 min) twice to remove the platelet-rich plasma. The cell pellet was washed by centrifugation and resuspended in HBSS without Ca²⁺ or Mg²⁺. Histopaque 1077 was layered under the cell suspension and centrifuged at 400×g for 30 min to obtain the buffy coat. The interfacial buffy coat, containing monocytes and lymphocytes, was removed and saved. The buffy coat was washed twice with HBSS without Ca²⁺ or Mg²⁺ by centrifugation. The cell pellet (4–6×10⁸ cells/30 mls) was resuspended in iso-osmotic media (RPMI-1640, 10% heat inactivated fetal bovine serum (FBS), 0.2 mM L-glutamine, 2.5 mM HEPES) and layered over an equal volume of 46% Percol mixture (10×PBS/Percol; 9.25/0.75) and 54% iso-osmotic media and centrifuged for 30 min at 1000×g (Marshall and Roshak, Biochem. Cell Biol. 71:331–339, 1993). The monocyte population located at the interface of the Percoll gradient was removed and washed twice in HBSS without Ca²⁺ or Mg²⁺. This resulted in a greater than 85–90 % pure monocyte population as assessed by differential staining.

Measurement of Stimuli-Induced Eicosanoid Release. Monocytes (5×10⁶/ml) were incubated as a suspension in serum-free RPMI-1640 medium containing the vehicle DMSO (<1%) or drug for 30 min at 27° C. after which vehicle or stimuli was added for the indicated time. The stimulating agent is solubilized in DMSO and appropriate vehicle controls were included in all experiments. The amount of stimuli was chosen from the linear portion of a concentration versus product curve usually representing 60–80% maximal stimulation over the indicated incubation time at 37° C. (A23187, 1 µM,(15 min). The reaction was terminated by reduction of pH through addition of citric acid and centrifugation (10 min, 400×g, 4° C.). Cell viability was monitored before and after experiments using trypan blue exclusion. The cell-free media was decanted and stored at −70° C. until analyzed. Prostaglandin $E_2$ and $LTC_4$ were directly measured in cell-free media using enzyme immunoassay (EIA) kits purchased from Caymen Chemical Co. (Ann Arbor, Mich.). Sample or standard dilutions were made with appropriate media and analyzed in triplicate. Results were obtained by extrapolation from a standard curve prepared in the media and expressed as pg or ng/ml of sample.

A representative compound herein which demonstrated positive activity in this assay was:
2-[2-[[[[3,5-Bis(trifluoromethyl)phenyl]amino]carbonyl]amino]-4-(trifluoromethyl)-phenoxy]-5-(1,1-dimethylpropyl)benzenesulfonic acid For instance, the above noted a compound demonstrated (as an $IC_{50}$) $PGE_2$>10 uM, and for $LTC_4$1 uM.

IN VIVO ASSAYS

Assays (g and h): Assay (Method) for TPA (assay g)or Arachidonic acid (assay h)-induced Inflammation
Animals:
Male Balb/c inbred mice were obtained from Charle River Breeding Laboratories (Kingston, N.Y.). Within a single experiment mice (22–25 g) were age-matched. These in vivo experiments typically involved use of 5–6 animals/group.
(g) TPA-induced Mouse Ear Inflammation:
Assay of Ear Edema
TPA (12-0-tetradecanoylphorbol 13-acetate) (Sigma Chemical Company) in acetone (4 mg/20 ml) was applied to the inner and outer surfaces of the left ear of BALB/c male mice. The thickness of both ears was then measured with a dial micrometer (Mitutoyo, Japan) at both 2 and 4 hours after treatment, and the data expressed as the change in thickness ($10^{-3}$ cm) between treated and untreated ears. The application of acetone did not cause an edematous response; therefore, the difference in ear thickness represented the response to the TPA. After measuring the edema, the inflammed left ears were removed and stored at −70° C. until they were assayed for MPO (myeloperoxidase) activity where appropriate.
Assay of Myeloperoxidase (MPO) in Inflamed Ear Tissue:
On the day of the assay, partially thawed ear tissues were minced and then homogenized (10% w/v) with a Tissumizer homogenizer (Tekmar Co.) in 50 mM phosphate buffer (pH 6) containing 0.5% HTAB. The tissue homogenates were taken through three cycles of freeze-thaw, followed by brief sonication (10 sec). The method of Bradley et al. was used with modifications as described. The appearance of a colored product from the MPO-dependent reaction of o-dianisidine (0.167 mg/ml; Sigma) and hydrogen peroxide (0.0005%; Sigma) was measured spectrophotometrically at 460 nm. Supernatant MPO activity was quantified kinetically (change in absorbance measured over 3 min, sampled at 15-sec intervals) using a Beckman DU-7 spectrophotometer and a Kinetics Analysis package (Beckman Instruments, Inc.). One unit of MPO activity is defined as that degrading one micromole of peroxide per minute at 25° C.

Statistics;
Statistical analysis was done using Student's "t" test. The $ED_{50}$ are values which cause a 50% inhibition of the inflammatory response and are calculated by regression analysis of the dose response data.
(h) Arachidonic acid induced ear inflammation assay
Arachidonic acid is dissolved in acetone (1 mg/ear) to the left ear of BALB/c male mice. The thickness of both ears was measured with a constant pressure thickness guage 1 hour after treatment and the data expressed as the change in thickness between treated and untreated ears. Test compounds or vehicle are given at the time of AA application. The inflammatory cell infiltration is measured by MPO activity as described above in the TPA ear edema assay. After the edema measurements are made, the inflamed ears are removed and assayed for MPO activity.

The anti-inflammatory effect of various standard inhibitors topically administered in the AA and TPA induced mouse car edema model were measured for dexamethasone, scalaradial and Wyeth's compound WY 50,295 at does of 0.2, 0.1 and 0.3 respectively. The TPA % change in edema was −50 (p<0.001), −46 (p<0.01) and −18 (ns) respectively; for AA the change was −10 (ns), −11(ns) and −50 (p<0.001). The change in MPO for TPA model was −54 (p<0.001), −65 (p<0.001) and −36 (p<0.05) respectively; for AA it was 0 (ns), −33 (ns) and −90 (p<0.001). One hypothesis is that the AA administration to the car overrides the need for $PLA_2$ mediated liberation of substrate for subsequent proinflammatory lipid mediator generation or AA mobilization by CoA-IT. In this case an inhibitor of an AA-metabolizing enzyme should be effective while and inhibitor of $PLA_2$ would be ineffective. As noted above, scalaradial and dexamethasone have little or no effect in the AA car model at concentrations which were effective in the TPA ear model. This can be contrasted to the activity of the selective 5-LO inhibitor WY 50,295 which strongly inhibits inflammation in response to AA. The AA car model therefore responds well to compounds that exhibit 5-LO inhibitory action and appears to be uneffected by putative $PLA_2$ inhibitors. This model therefore provides a unique mol with which the contribution of the 5-LO inhibition to the in vivo anti-inflammatory activity of various compounds can be separated from LMW-$PLA_2$ inhibition.

The compounds of Formula (II), 2-[2-[[[[3,5-Bis(trifluoromethyl)phenyl]amino]carbonyl]amino]-4-(trifluoromethyl)-phenoxy]-5-(1,1-dimethylpropyl)benzenesulfonic acid, and 2-[2-[3-(4-Chloro-3-trifluoromethylphenyl)ureido]-4-trifluoromethylphenoxy] -5-(1,1-dimethylpropyl)benzenesulfonic acid; demonstrated a positive inhibition in these animal models.

Specifically in the TPA ear model at 50 mg/ear topically both compounds demonstrated roughly equipotent inhibitors of the inflammatory cell infiltration. The compound 2-[2-[3-(4-Chloro-3-trifluoromethylphenyl)ureido]-4-trifluoromethylphenoxy]-5-(1,1-dimethylpropyl)-benzenesulfonic acid demonstrated, for edema, an $ED_{50}$ of 0.32 mg/ear and for MPO and $ED_{50}$ of 0.36 mg/ear and 2-[2-[[[3,5-Bis(trifluoromethyl)phenyl]amino] -carbonyl]amino]-4-(trifluoromethyl)-phenoxy]-5-(1,1-dimethylpropyl)benzenesulfonic acid, demonstrated, for edema, 0.87 mg/ear and for MPO 0.25 mg/ear.

In addition, for the AA ear model the compound 2-[2-[3-(4-Chloro-3-trifluoromethylphenyl)ureido]-4-trifluoromethylphenoxy]-5-(1,1-dimethylpropyl)-benzenesulfonic acid demonstrated activity of −22 @ 1 mg and 2-[2-[[[3,5-

Bis(trifluoromethyl)phenyl]amino] -carbonyl]amino]-4-(trifluoromethyl)-phenoxy]-5-(1,1-dimethylpropyl)benzenesulfonic acid, demonstrated activity of −25 @ 1 mg in direct contrast to the information provided above for Dexamethasone, Scalaradial and the Wyeth compound.

Thus this demonstrates a clear utility in the treatment of topically administered diseases associated with inflammation as noted herein such as, but not limited to, inflammatory bowel disease, contact dermatoses, actinic keratosis, psoriasis, or conjuctivitis.

Assay (I): DMPM Assay for LMW-PLA$_2$

The DMPM assay is used to distinguish specific catalytic inhibitors from nonspecific agents. Catalysis by the low molecular weight PLA$_2$ involves a two step process where the enzyme first binds to the water-lipid interface and then binds and hydrolyzes a single molecule of phospholipid at the active site. Binding to the interface is a reversible process. The relative rates of interfacial binding and substrate hydrolysis determine the kinetics in a particular substrate system. If a compound affects the surface charge, or the "quality" of the interface, inhibition may result as the enzyme will spend less time at the interface, rather than because hydrolysis is inhibited. DMPM has been shown to bind low molecular weight PLA$_2$ to its water-lipid interface very tightly so that the hydrolytic reaction becomes completely processive relative to the interfacial binding. That is, many hydrolytic cycles (essentially an infinite number) occur before the enzyme falls off the surface. Because interfacial binding involves a fairly large part of the enzyme surface as well, this tight binding is unlikely to be affected by reasonable concentrations (less than 10 mole %) of added inhibitors. Using the DMPM substrate eliminates the artifacts that have been intrinsic to more conventional PLA$_2$ assays where the interfacial binding step is an important factor in the reaction kinetics.

Linear inhibition in the DMPM assay, according to a kinetic model analogous to a Dixon plot, implies a specific enzyme interaction but cannot distinguish between competitive and non-competitive inhibition. Results are given as Xi$_{50}$, or mole percent relative to the lipid substrate required for 50 % inhibition.

Preparation of Substrate:

0.1 mg per assay DMPM, weigh out and dissolve in CHCl$_3$ 5 mL [$^3$H]DPPC per assay, place in silanized 13×100 tube add DMPM in CHCl$_3$ and dry down under Argon, resuspend in no more than 1 mL water, sonicate at power setting 10 for 1.5 min., let stand at room temperature for 5–10 min., adjust the volume to 50 uL per assay, and aliquot into silanized 12×75 tubes.

Assay:

Add 50 uL DMPM/DPPC as prepared above, and inhibitor (determine in mole fraction, add in water or DMSO), heat to 50° C. for 5–10 min., add water equilibrated to same temperature if needed, add 150 uL Ca mix (1.2 mL 0.12M CaCl$_2$, 0.6 mL 0.4M HEPES pH 8.0, 10.2 mL water), cool to room temperature (15 min.). Start assay by addition of the enzyme, vortexing enzyme into the assay. Quench by addition of 5 uL 5N HCl and extract with 2×0.5 mL chloroform:methanol (2:1). Dry down extract, resuspend in 0.5 mL hexane:ethyl acetate:acetic acid (80:20:1) and apply to conditioned 3 mL Si column (condition with 1 mL hexane). Elute with 2.5 mL same solvent into scintillation vials, add 7 mL of the cocktail and count by any acceptable well known means.

Representative compounds of Formulas (I) and (II) which have shown positive activity in the above noted assay are:
2-[2-[3-(4-Chloro-3-trifluoromethylphenyl)ureido]-4-trifluoromethylphenoxy]-4,5 -dichlorobenzene sulfonic acid;

2-[2-[[[3,5-Bis(trifluoromethyl)phenyl]amino]carbonyl]amino]-4-chlorophenoxy]-5 -chlorobenzenesulfonic acid, and preferably the monosodium salt thereof;

5-Chloro-2-[2-(3-(3,5-di-trifluoromethylphenyl)ureido)-4-trifluoromethylphenyl)thio]benzenesulfonic acid;

5-(1,1-Dimethylpropyl)-2-[4-(trifluoromethyl)-2-[[[[3-(trifluoromethyl)phenyl]amino]carbonyl]amino]-phenoxy] benzenesulfonic acid, and preferably the monosodium salt thereof;

2-[2-[3-(4-Chloro-3-trifluoromethylphenyl)ureido]-4-trifluoromethylphenoxy]-5-(1,1-dimethylpropyl)benzenesulfonic acid;

2-[2-[[[[3,5-Bis(trifluoromethyl)phenyl]amino]carbonyl]amino]-4-(trifluoromethyl)phenoxy]-5-(1,1-dimethylpropyl)benzenesulfonic acid;

5-Chloro-2-[(4-chloro-2-(3-(4-chloro-3-trifluoromethylphenyl)ureido)phenyl)thio]benzenesulfonic acid; and 5-Chloro-2-(4-chloro-2-(2-(3-chlorophenoxy)-5 -trifluoromethylphenylaminocarbonylamino)phenyoxybenzene sulfonic acid.

As used herein, various abbreviations and explanations are as follows: [$^3$H], a molecule that contains tritium atoms, a radioactive isotope; A23187, a compound that allows free entry of calcium into a cell; AA, arachidonic acid; arachidonate, arachidonic acid contained within a phospholipid; free arachidonic acid, arachidonic acid that is not contained within a phospholipid; [$^2$H$_8$]arachidonic acid, the form of arachidonic acid labeled with 8 deuterium atoms, a stable isotope; 1-alkyl, 1-O-alkyl; 1-alkenyl, 1-O-alk-1'-enyl; BSA, bovine serum albumin; CoA, coenzyme A; CoA-IT, CoA-independent transacylase; DTr, dithiothreitol; EGTA, [ethylenebis(oxyethylenenitrilo)]tetra acetic acid, a calcium chelator; GPC, sn-glycero-3-phosphocholine; EDTA, a metal ion chelator; GPE, sn-glycero-3-phosphoethanolamine; GC/MS, gas chromatography and mass spectrometry; 5HETE, 5(S)-hydroxyeicosa-6,8,11,14-tetraenoic acid; 15HETE, 15 (S)-hydroxyeicosa-5,8,11,13-tetraenoic acid; HL-60, American Type Tissue Culture designated cell line similar to a monocyte; LTB$_4$, leukotriene B$_4$; LTC$_4$, leukotriene C$_4$; LTD$_4$, leukotriene D$_4$; lyso PAF, 1-alkyl-2-lyso-GPC, lyso platelet-activating factor; PLA$_2$, phospholipase A$_2$; PBS, phosphate buffered saline; PAF, platelet activating factor, 1-alkyl-2-acetyl-GPC; PL, phospholipid; PC, phosphatidylcholine; PE, phosphatilylethanolamine, PI, phosphatidylinositol; PMN, polymorphonuclear neutrophilic cell, neutrophil; PS phosphatidylserine; Rf, the distance a compound travels as a fraction of the solvent front; TLC, thin layer chromatography; U937, American Type Tissue Culture designated cell line similar to a monocyte.

The above description fully discloses the invention including preferred embodiments thereof. Modifications and improvements of the embodiments specifically disclosed herein are within the scope of the following claims. Without further elaboration, it is believed that one skilled in the art can, using the preceding description, utilize the present invention to its fullest extent. Therefore, the Examples herein are to be construed as merely illustrative and not a limitation of the scope of the present invention in any way. The embodiments of the invention in which an exclusive property or privilege is claimed are defined as follows.

What is claimed is:

1. A method for treating an inflammatory disease or disorder in a mammal in need thereof which method comprises administering to said mammal an effective amount of a compound of Formula (I)

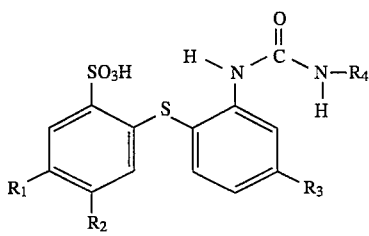

(I)

wherein

R$_4$ is a phenyl substiuted one to two times independently with chlorine or CF$_3$;

R$_1$ is chlorine;

R$_2$ is hydrogen or chlorine;

R$_3$ is chlorine or CF$_3$;

provided that when R$_1$ and R$_2$ are both chlorine then R$_3$ is CF$_3$;

and pharmaceutically acceptable salts thereof.

2. The method according to claim 1 wherein the inflammatory disease or disorder is allergic rhinitis, ischemia, reperfusion injury, arthritis, inflammatory bowel disease, Crohn's disease, ulcerative colitis, asthma, adult respiratory distress syndrome, analphylaxis, actinic keratosis, psoriasis, contact dermatitis, or pyresis.

3. The method according to claim 1 wherein the inflammatory disease or disorder is mediated by lipid inflammatory mediators, arachidonic acid, its metabolites and/or platelet activating factor (PAF).

4. The method according to claim 3 wherein the lipid inflammatory meditors are inhibited by the an inhibitor of the enzyme phospholipase A$_2$ (PLA$_2$) or Coenzyme A independent transacylase (CoA-IT).

5. The method according to claim 1 wherein the compound, or pharmaceutically acceptable salt thereof, is 4,5-Dichloro-2-[4-trifluoromethyl-2-(3-trifluoromethyl-4-chlorophenyl)ureido)phenyl)thio]benzenesulfonic acid;

4,5-Dichloro-2-[3-(3,4-dichlorophenyl)ureido]-4-trifluoromethylphenyl)thiobenzenesulfonic acid;

5-Chloro-2-[2-(3-(3,5-di-trifluoromethylphenyl)ureido)-4-trifluromethylphenyl)thio]benzenesulfonic acid;

5Chloro-2-[(4-chloro-2-((3-(5-chloro-3-trifluoromethylphenyl)ureido)phenyl)thio]benzenesulfonic acid;

5-Chloro-2-[(4-chloro-2-[3-(2,4-dichlorophenyl)ureido)phenyl)thio]benzenesulfonic acid; or 5-Chloro-2-[(4-chloro-2-(3-(4-chloro-3-trifluoromethylphenyl)ureido)phenyl)thio]benzenesulfonic acid.

* * * * *